United States Patent
Warila

(10) Patent No.: US 7,594,935 B2
(45) Date of Patent: Sep. 29, 2009

(54) PROSTHETIC DEVICE CONTOURING AND ALIGNMENT METHOD AND APPARATUS

(76) Inventor: Jeffery W. Warila, 97 N. Hayden Bay Dr., Portland, OR (US) 97217

( * ) Notice: Subject to any disclaimer, the term of this patent is extended or adjusted under 35 U.S.C. 154(b) by 472 days.

(21) Appl. No.: 11/355,378

(22) Filed: Feb. 15, 2006

(65) Prior Publication Data

US 2006/0179935 A1    Aug. 17, 2006

Related U.S. Application Data

(60) Provisional application No. 60/653,351, filed on Feb. 15, 2005.

(51) Int. Cl.
*A61F 2/80* (2006.01)
(52) U.S. Cl. .............................. 623/32; 623/33; 623/34
(58) Field of Classification Search ................... 623/32, 623/33, 34; 73/172
See application file for complete search history.

(56) References Cited

U.S. PATENT DOCUMENTS

| | | | | |
|---|---|---|---|---|
| 2,663,475 A | * | 12/1953 | Mcinerney et. al. | 53/114 |
| 3,616,690 A | * | 11/1971 | Harden | 73/172 |
| 4,014,398 A | * | 3/1977 | Gresko | 600/592 |
| 4,986,802 A | * | 1/1991 | Scoville et al. | 475/346 |
| 5,165,660 A | * | 11/1992 | Engel et al. | 254/126 |
| 5,609,162 A | | 3/1997 | Blumentritt et al. | 128/782 |
| 5,658,353 A | * | 8/1997 | Layton | 623/34 |
| 5,728,165 A | * | 3/1998 | Brown, Sr. | 623/33 |
| 5,750,937 A | * | 5/1998 | Johnson et al. | 177/25.11 |
| 6,437,257 B1 | * | 8/2002 | Yoshida | 177/199 |
| 7,107,832 B2 | | 9/2006 | Blumentritt et al. | 73/172 |
| 2004/0068337 A1 | * | 4/2004 | Watson et al. | 700/98 |
| 2006/0089657 A1 | * | 4/2006 | Broers et al. | 606/102 |
| 2006/0173553 A1 | * | 8/2006 | Holzer et al. | 623/32 |

* cited by examiner

*Primary Examiner*—Andre J Allen
(74) *Attorney, Agent, or Firm*—Kolisch Hartwell, PC

(57) ABSTRACT

A method for recording information regarding a balance orientation of a limb-receiving member covering a residual limb of an amputee by applying force to a movable alignment device, transmitting light onto the limb-receiving member to define a first balance plane through the limb-receiving member.

10 Claims, 6 Drawing Sheets

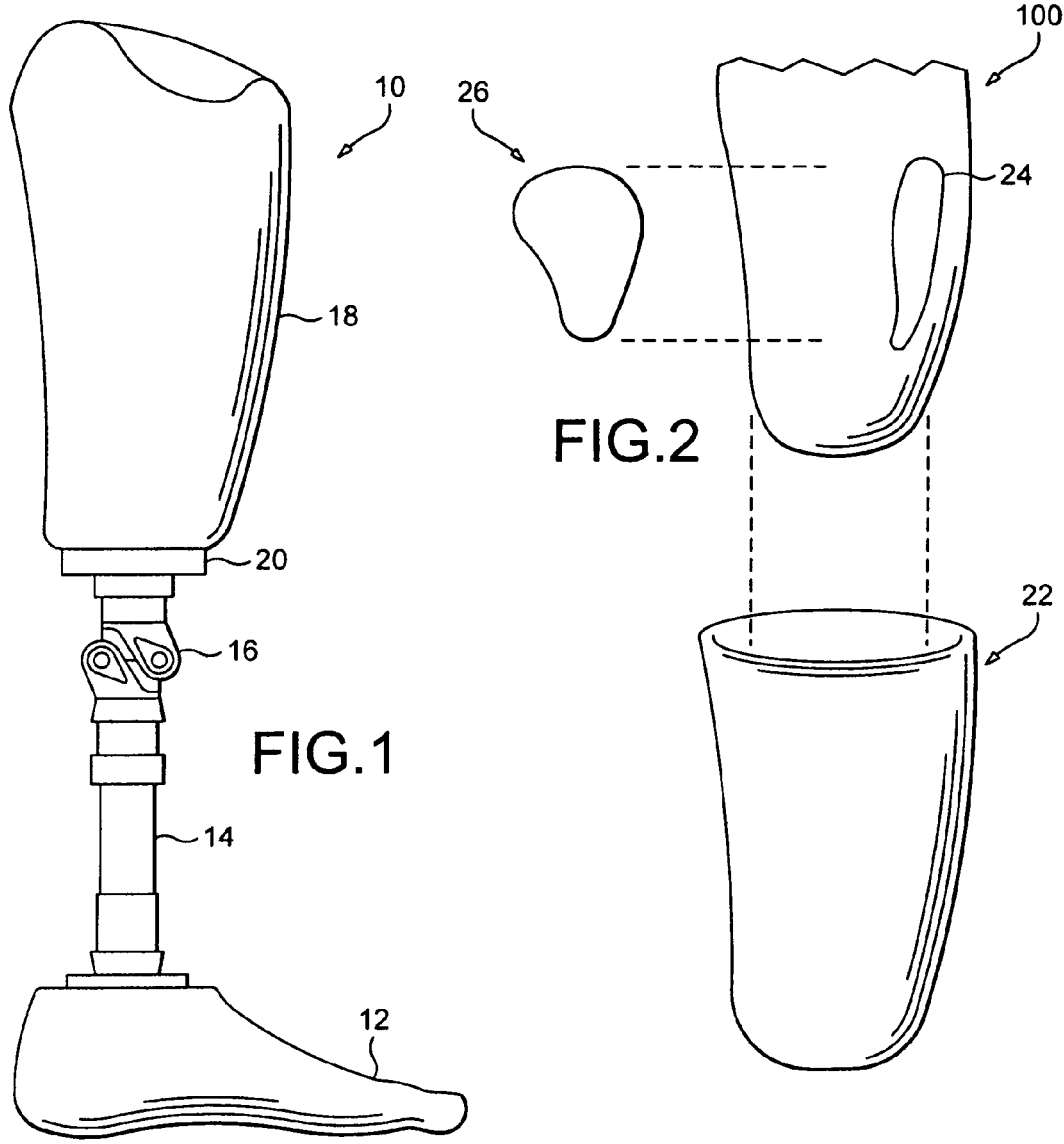
FIG.1
FIG.2
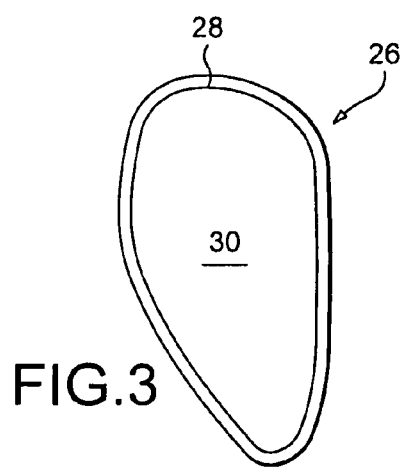
FIG.3
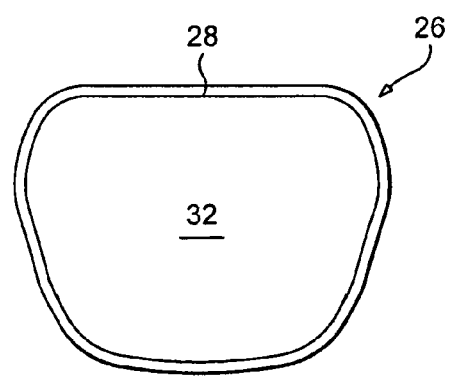
FIG.4

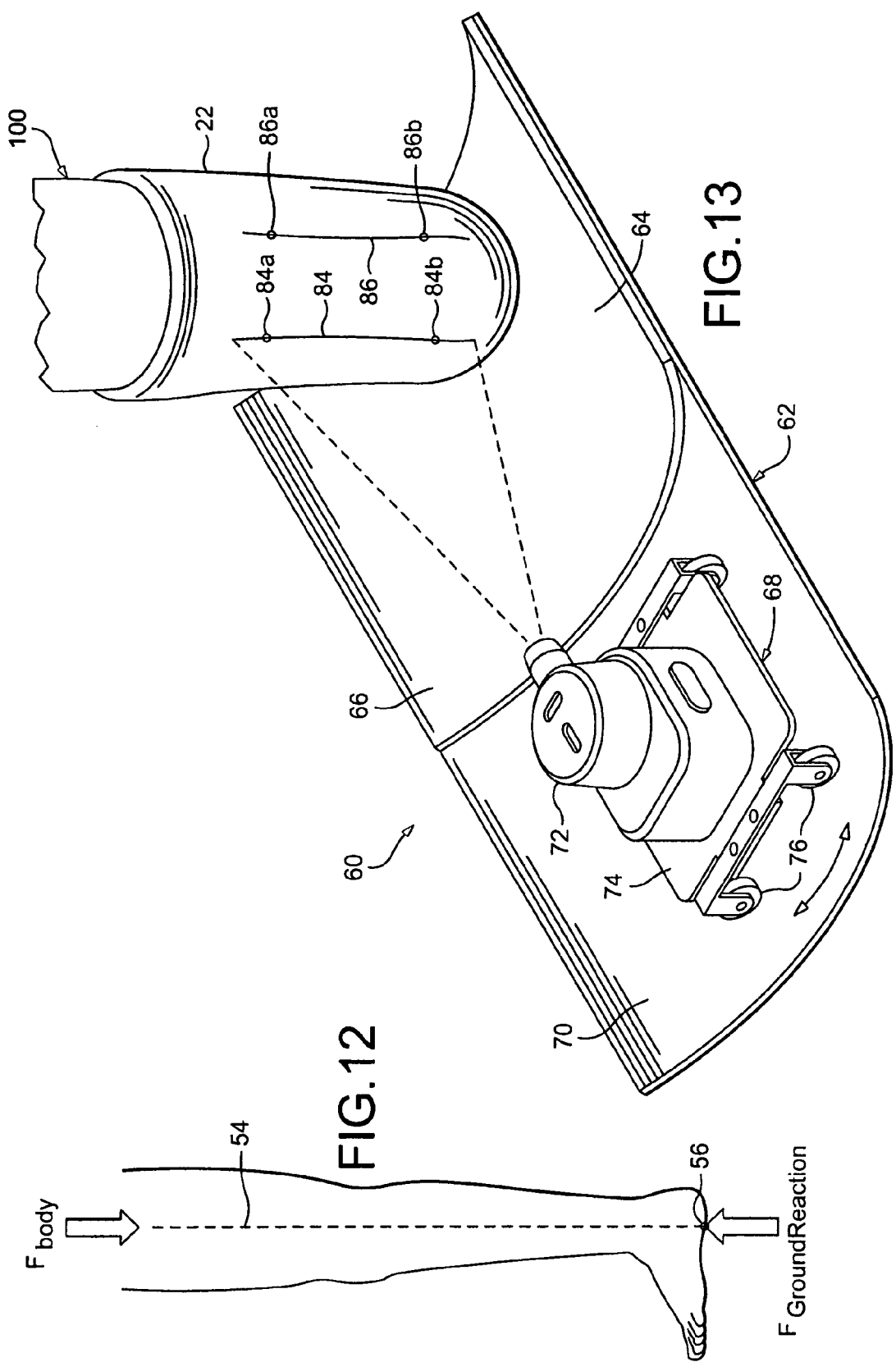

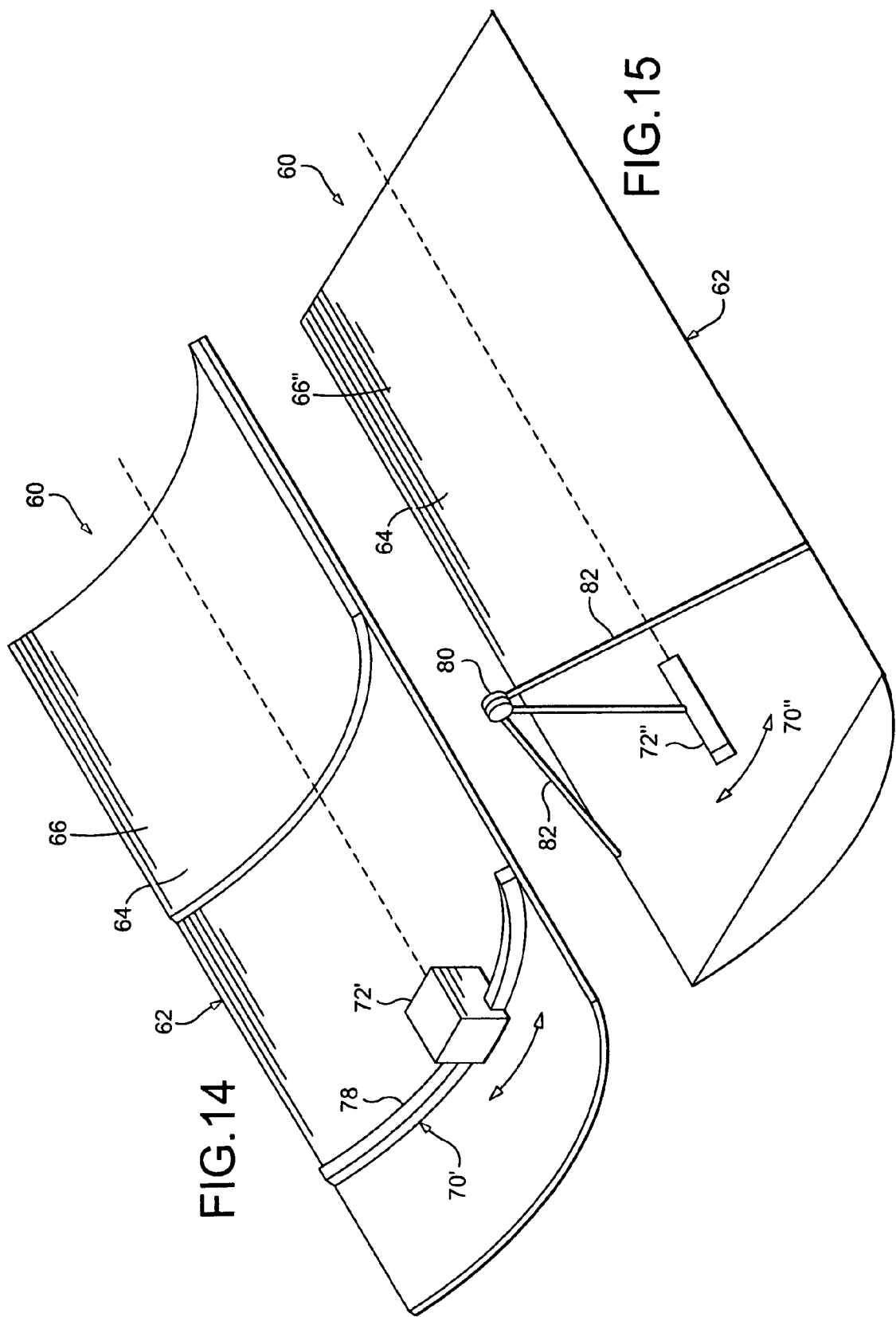

PROSTHETIC DEVICE CONTOURING AND ALIGNMENT METHOD AND APPARATUS

CROSS-REFERENCE TO RELATED APPLICATION

This application claims priority from U.S. Patent Application Ser. No. 60/653,351, which was filed on Feb. 15, 2005 and entitled "Prosthetic Device Contouring and Alignment Method and Apparatus," the complete disclosure of which is incorporated herein by reference for all purposes.

TECHNICAL FIELD

This disclosure relates generally to prosthetic devices, and more particularly, to prosthetic devices for use by lower extremity amputees. The disclosed method and apparatus may assist clinicians in properly shaping and aligning the components of the prosthetic device during fabrication.

BACKGROUND OF THE INVENTION

A prosthetic device, or prosthesis, is an artificial substitute for a part of the body such as a limb. Most prosthetic devices have sockets to attach the device to the amputee's residual limb. One of the challenges of socket design is to provide proper orthopedic contouring and positioning of the prosthetic device relative to the user's body.

Socket geometry provides support surfaces necessary for weight transfer. The socket must be able to appropriately transfer body weight onto load bearing areas and provide relief space for bony or sensitive areas. The socket therefore may not perfectly correspond to the shape of the residual limb once modifications have been made to the socket to account for sensitive areas and loading requirements. Modifications to the socket geometry may be made by using an ink pencil to mark the bony prominences and sensitive areas on the residual limb. These markings may be transferred to the cast and subsequent plaster model, which may be contoured according to the markings by the prosthetist. A temporary prosthesis then may be assembled by connecting the socket with other structural members, such as a pylon for the lower portion of the leg and a foot member. A provisional alignment may be made by estimating the appropriate overall length of the prosthesis and the relative orientation of each component. Minor adjustments then may be made while the user stands or walks.

Such a method generally requires significant time as the plaster model is modified by hand, a temporary socket is formed, the temporary socket and prosthetic alignment is tested by the user, and adjustments are made to fine tune the fit of the socket and alignment of prosthetic components.

BRIEF DESCRIPTION OF THE DRAWINGS

FIG. 1 is a side view of components of an above-the-knee prosthesis, including a socket, an artificial knee structure, an artificial shin structure, and an artificial foot structure.

FIG. 2 is a side view of a limb-receiving member in the form of a cast, pressure pads for modifying the cast while it is formed, and an amputee's residual limb, including markings for further shape adjustment.

FIG. 3 is a front view of a pressure pad appropriate for modifying the cast contour over the femoral triangle.

FIG. 4 is a front view of a distal lateral femur pad appropriate for modifying the cast contour over the distal end of the femur.

FIG. 12 illustrates a position of standing postural balance.

FIG. 13 is a perspective view illustrating an alignment device that may be used to designate a balance position on a residual limb cast, the alignment device including a light source mounted on wheels to mark a balance line on the cast when the cast bears on the alignment device.

FIG. 14 shows an alignment device, similar to that of FIG. 13, but with a light source mounted on a track.

FIG. 15 shows an alignment device with a pendulum light source.

DETAILED DESCRIPTION

Figure 5:
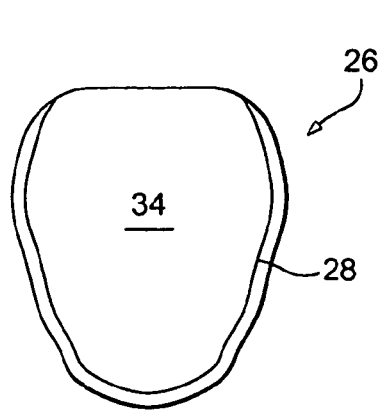
FIG. 5 is a front view of an ischial pad appropriate for modifying the cast contour over the ischium.

The present disclosure provides a method and apparatus for properly forming and aligning a prosthetic device, namely a lower extremity prosthesis. One such prosthesis is shown in FIG. 1, the prosthesis being indicated generally at 10.

As indicated, the prosthesis may be considered to include an artificial foot structure 12, an artificial shin structure 14, an artificial knee structure 16, and a socket assembly 18. The artificial knee structure may be coupled to the socket assembly with an alignment block 20, or other suitable support structure. Placement of the alignment block on the socket assembly determines balance and load bearing of the prosthetic device.

Although the depicted embodiment is incorporated into a prosthesis for above-the-knee amputees, the prosthesis could be modified by removing the artificial knee structure and shifting the socket assembly downward to accommodate a below-the-knee amputee. Further, it will be appreciated that the prosthesis may be covered by artificial skin made from a material such as rubber so as to more closely resemble a natural leg.

In the present embodiment, socket assembly 18 takes the form of a hard outer socket. The outer socket may be formed from a rigid material such as a hard plastic and may be adapted to maintain a substantial portion of a residual limb stable while a user is standing or moving. A soft socket may fit within the hard socket to better distribute pressure on the residual limb, and to allow for volume fluctuations of the residual limb. The soft socket may include a neoprene or nonporous polyurethane gel liner and/or a cotton sock. Since the soft socket covers the distal end of the residual limb, it may serve to provide further protection to the residual limb tissues.

When forming the outer socket, a prosthetist examines the amputee's residual limb, shown generally at 100 in FIG. 2, to identify bony prominences or other sensitive areas to be protected, and to identify areas that may be used for load bearing contact with the prosthesis. The prosthetist may cover the residual limb with a limb-receiving member such as cast 22. It should be appreciated that although the present invention is described in the context of a cast for use in preparing a prosthetic socket, the method and apparatus also is suitable for use in recording information regarding a balance orientation of a traditional clear diagnostic socket or even a definitive laminated acrylic socket.

As described below, the cast may be contoured to achieve desired load-bearing characteristics. Once contoured, the cast may be used to produce a limb model, and the limb model may be used to form hard socket 18. Markings, typically via ink pencil, may be made on the residual limb and absorbed by the cast, or made on the cast after it is formed. An example of a marking used to modify a cast and resulting socket is shown generally at 24 in FIG. 2.

In accordance with the present method, sensitive areas on the residual limb may be protected before casting material (such as plaster gauze like that used for setting bone fractures) is applied. Thus, when a cast is made of the residual limb, there is adequate relief space for the sensitive areas and the resulting socket will not apply inappropriate pressure to the residual limb. The cast also may be modified as the cast sets, via hand manipulation by the prosthetist to apply more pressure to weight tolerant areas, and thus to induce load bearing in those areas. As described herein, the cast-covered residual limb and cast may be placed in a balance orientation, and the cast marked to accommodate proper placement and alignment of prosthetic components on the prosthesis formed using the cast.

Once the cast is properly contoured, and any desired measurements are made, the cast is removed. Later, the cast may be filled with plaster to create a positive limb model from which the hard socket is formed.

As shown in FIG. 2, a variety of pressure pads 26 may be used before or after casting to modify the socket contours, either relieving or inducing pressure from the resulting socket on the residual limb. Use of such pads may reduce the need for ink pencil markings, and may produce and produce a more appropriately shaped socket after a single cast is formed. The pads may be a dense, low-friction material, such as soft-cell foam.

The pressure-relieving pads may be applied to the sensitive areas before the casting material is applied, as illustrated in FIG. 2. The resulting cast 22 therefore may provide more space to the residual limb in the sensitive areas, thereby alleviating pressure that the resulting socket would otherwise apply.

The pressure-inducing pads may be applied to the interior of cast 22 after the casting material has set. The positive limb model formed with the cast thus may be made narrower in the selected weight-tolerant areas, thereby decreasing space in the resulting socket to increase pressure on the residual limb in such weight-tolerant areas.

The pressure pads may be secured to the residual limb, or cast interior, using an adhesive backing such as double-sided tape, or any other suitable method of temporarily affixing the pads. As indicated generally in FIGS. 3-11, The edges of pads 26 may be beveled (shown at 28) so that the pads blend with the contours of the residual limb and/or cast to produce a smooth transition. Bevels 28 may be cut at any suitable angle that provides a smooth taper. For example, the bevel may be cut to provide a smooth taper over a distance of 1-inch to 2-inches. The pads may be generally planar and approximately ⅛-inch thick, although it should be appreciated that the thickness may be varied depending on the pressure needs for a particular area of application, or a particular amputee's needs. The pads may also be configured to fit a variety of body shapes and sizes. Consequently, the pads may be provided in a variety of sizes, and/or may be configured to be modified by cutting a section out of the pad, as will be described in more detail below.

One example of a weight tolerant area is Scarpa's area, also known as the femoral triangle, which is located on the upper, inner thigh, adjacent the pelvis. As shown in FIG. 3, the depicted pressure-inducing femoral triangle pad 30 may be used on either the left or right thigh, depending on which side of the pad the adhesive backing is applied. This pressure-inducing pad may be applied to the interior of the cast. This pad may be an eighth of an inch thick with the dashed lines of FIG. 3 depicting the beveled edge 28 that may be associated with this pad. The interior line alternatively may indicate a cut line so that the pad may be scaled to fit the pad to a variety of amputee sizes. Pressure pads may be contoured to correspond to predetermined anatomical landmarks. For example, the pad of FIG. 3 is shaped to substantially overlap the femoral triangle while providing a smooth transition to surrounding areas.

FIG. 4 illustrates another example of a pressure-inducing pad, in particular, distal lateral femoral pad 32 is configured to overlap the lower, outer thigh. This pressure-inducing pad may be applied to the interior of the cast. This pad may be approximately ⅛-inch thick. As shown by interior line, distal lateral femoral pad 32 may have a beveled edge around the entire perimeter of the pad.

Still another example of a pad that induces pressure is depicted in FIG. 5. Ischial pad 34 may be configured to overlap the area of the cast that corresponds to the ischial tuberosity of the pelvis. Consequently, ischial pad 34 may have a full thickness, such as approximately ⅛-inch, at the top of the pad with beveled edges extending along the bottom and sides, as shown by the interior line. This pressure-inducing pad may be applied to the interior of the cast.

Figure 6:
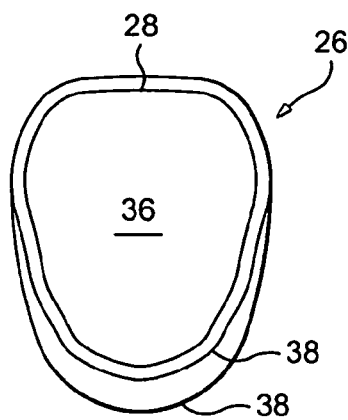
FIG. 6 is a front view of a popliteal pad appropriate for modifying the cast contour adjacent the popliteal fossa.

As shown in FIG. 6, pressure-inducing popliteal pad 36 may be placed on the interior of the cast corresponding to the back of the knee to increase pressure against the popliteal fossa. Popliteal pad 36 may have a variable length, as shown at 38. This pad may be approximately ⅛-inch thick. As shown by interior line, popliteal pad 36 may have a beveled edge around the entire perimeter of the pad.

Figure 7:
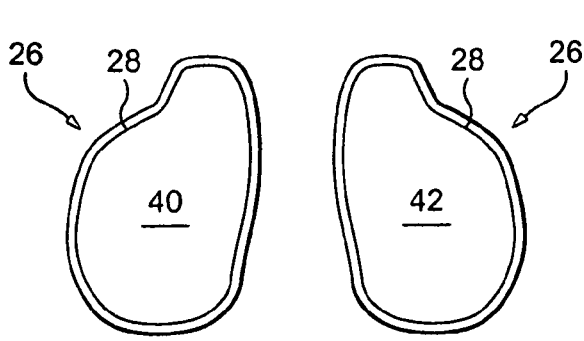
FIG. 7 is a front view of a pair of interoseous pads appropriate for modifying the cast contour adjacent the proximal juncture of the tibia and fibula.

FIG. 7 illustrates pressure-inducing interoseous pads, including a left interoseous pad 40 and a right interoseous pad 42. The interoseous pads may be placed on the interior of the cast corresponding to the front of the knee where the interoseous ligament connects the tibia and the fibula. The interoseous pads may be manufactured specifically for a right or left side. Alternatively, a single pad may be used with double-sided tape on both sides, thereby being reversible. These pads may be approximately ⅛-inch thick. As shown by interior line, the interoseous pads may have a beveled edge around the entire perimeter of the pads.

Figure 8:
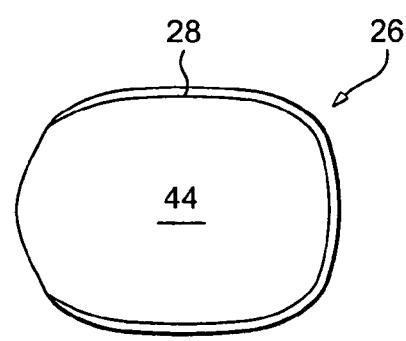
FIG. 8 is a front view of a patellar relief pad appropriate for modifying the cast contour adjacent the patella.

FIG. 8 illustrates an example of a pressure-relieving pad. Patellar relief pad 44 may have a thickness approximately ⅛-inch and be applied to the residual limb in layers. In some examples, this pad may have a thickness of approximately ¼-inch along an edge of the pad with beveled edges extending along the other sides. The greater thickness may assist in relieving pressure on bone spurs on the residual limb in the area of the knee. This pressure-relieving pad may be applied to the residual limb prior to casting.

Figure 9:
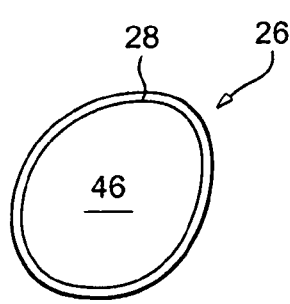
FIG. 9 is a front view of a fibula head pad appropriate for modifying the cast contour adjacent the head of the fibula.

An example of a pressure-relieving fibula head pad 46 is shown in FIG. 9. This pressure-relieving pad may be applied to the residual limb prior to casting. The fibula head pad 46 may be applied to the lateral side of the knee to limit pressure on the fibula. This pad may be approximately ⅛-inch thick. Fibula head pad 46 may have a beveled edge, as shown by interior line. In some examples, fibula head pad 46 may have a consistent thickness and may be cut to scale the pad to fit patients of different sizes.

Figure 10:
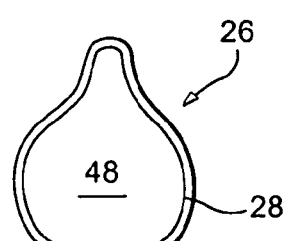
FIG. 10 is a front view of a distal tibia pad appropriate for modifying the cast contour over the distal end of the tibia.

FIG. 10 illustrates an example of a pressure-relieving distal tibia pad 48. Distal tibia pad 48 may be applied to the distal end of the tibia near the ankle prior to casting. The distal tibia pad may have a thickness of approximately ⅛-inch and a beveled edge, as shown by interior line.

Figure 11:
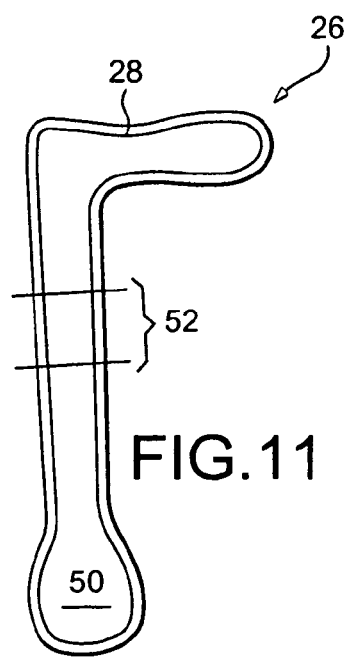
FIG. 11 is a front view of a pretibial pad appropriate for modifying the cast contour along the front of the tibia.

Still another example of a pressure-relieving pad is shown in FIG. 11. Pretibial pad 50 may be applied to the front of the tibia prior to casting to relieve pressure along this bony prominence. To scale pretibial pad 50, a section 52 may be cut out of the pad and the cut ends rejoined. The pad may have a beveled edge, as shown by interior line. As previously noted, the interior line alternately may indicate a cut line for further scaling.

Once the pressure-relieving pads are properly positioned on the residual limb, a thin sock or nylon may be pulled over the residual limb and pads. Casting material, such as plaster gauze like that used for setting bone fractures, may be applied over the sock to form an impression of the residual limb. After appropriate measurements are taken, and alignment markings are made, the cast may be removed. Pressure-inducing pads may then be applied to the interior of the formed cast to modify the negative model defined by the interior of the cast. A positive limb model (typically of plaster) may then be formed using the modified negative model. Prosthetic socket 18 may then be formed around the positive limb model. As noted above, the prosthetic socket may be formed of a hard plastic, which may be molded using known techniques, such as vacuum forming.

By accounting for sensitive areas at the beginning of the casting process, and modifying the cast interior prior to forming a positive limb model, the prosthetist may reduce the modifications needed to produce a comfortable socket for the amputee.

Although this casting process has been described with reference to the lower extremities, the process is also applicable to the upper extremities. For example, pressure pads 26 may be used to protect sensitive areas, such as bony prominences of the arm, while forming a cast for such a socket.

The cast may further be used with the following method and device to reduce the number of modifications needed to align the various components of a weight-bearing lower extremity prosthesis.

When fitting a lower extremity prosthesis, the various components of the prosthesis need to be properly aligned to ensure that the amputee maintains a normal standing posture and gait pattern. This may be accomplished by aligning the prosthetic components while the amputee is in a position of standing postural balance, as shown in FIG. 12. When standing, an individual is considered in perfect balance when the center of gravity of the body, generally indicated by $F_{Body}$, acting along dashed line 54, is directly over the center of pressure 56 of the ground reaction force, indicated by $F_{GroundReaction}$. By simulating this position, the prosthetic components may be aligned to mimic the amputee's natural posture and gait. For example, the length of a prosthetic leg may be adjusted so that the hips are level. The medial/lateral and anterior/posterior alignment of the prosthetic components, such as shin structure 14, also may be adjusted so that the prosthesis properly supports the upper body of the user.

Although commercially available sensors, such as force plates upon which an individual may stand, may be used to determine the relationship between the center of gravity and the center of pressure, the necessary equipment may be cost prohibitive to clinicians. Moreover, force plates may produce inaccuracies in determining this relationship as such equipment is affected by sheer and rotational stresses. Consequently, the following alignment device may be used in a method of determining a prosthetic alignment configuration that will place an amputee in postural balance.

As shown in FIGS. 13-15, alignment device 60 may include an adjustable base in the form of a balance member 62. The balance member may take the form of an arcuate plate configured to move relative to a supporting structure in response to an applied force. As indicated, balance member 62 may define a curved underside 64 that allows the base to roll to a balanced resting position on delivery of an applied force to an upper surface thereof. In such a configuration, balance member 62 is free to move along a supporting surface in response to a force applied by an amputee's cast-covered residual limb. The amputee generally need apply only enough force so that the amputee feels comfortably balanced when standing and the prosthetist is able to verify proper alignment of anatomical structures associated with standing postural balance. The orientation of the cast associated with standing postural balance will further be referred to as the balance orientation of the cast. Once in the balance orientation, the cast may be marked with reference designations (e.g. balance lines) that may be used to determine proper alignment of prosthetic components upon formation of the hard socket.

Balance member 62 may be formed of a rigid material, such as plastic or metal. In some embodiments, balance member 62 may have a deformable portion 66 defined by a material such as foam padding or the like. In operation, the amputee may rest his or her cast-covered residual limb on the upper surface of balance member 62, generally by placement of the cast-covered residual limb in a balanced orientation on deformable portion 66. Deformable portion 66 may account for minor variations in the contour of cast 22 so that variations in the exterior shape of the cast do not improperly affect determination of a balance position on the cast (e.g. the lowermost load-bearing position on the cast when the cast is in a balance orientation).

To assist in designating the balance position of the cast for prosthetic component alignment and assembly, a movable, self-leveling structure 68 may be used in combination with balance member 62. Self-leveling structure 68 may be movable relative to balance member 62 so that as the balance member moves in response to the force applied through the cast, the self-leveling structure automatically moves along a travel path 70 to maintain a predetermined alignment with the cast. As described below, in the present embodiment, self-leveling structure 68 is configured to place a balance line on a cast bearing on the balance member. The balance line corresponds with a substantially vertical plane passing through the lowermost point on the cast when the cast bears on the balance member in a balance orientation.

As shown in FIG. 13, self-leveling structure 68 may include a light source 72, or other marker, mounted to a platform 74. The platform may be fitted with a set of wheels 76, or other suitable travel structure suitable for low-friction movement along travel path 70. Light source 72 may be a Ryobi AIRgrip™ Laser Level or any other suitable light source or marker capable of designating a line on a cast. Light source 72 may be removably coupled to platform 74, or may be integrally formed with a set of wheels or other travel structure. Further, light source 72 may be rotatable relative to its platform 74 to vertically adjust the direction of the projected light.

In some embodiments, the light source (or marker) may travel along a track or groove on balance member 62. For example, as shown in FIG. 14, light source 72' travels along a low-friction track 78 that allows the light source to freely move across balance member 62 under the force of gravity as the balance member is rolled on underside 64. Track 78 may include one or more rails that define travel path 70'. Light source 72' may be permanently or removably coupled to balance member 62.

In still other embodiments, the light source may take the form of a pendulum suspended as shown in FIG. 15. Such a configuration provides a plumb-line system that rotates light source 72" about pivot 80. As shown, cross bars 82 may provide support structure from which light source 72" hangs and is free to pivot about pivot 80. As the balance member moves in response to a force applied through the cast, gravity moves light source 72" to remain aligned with the cast. As shown, the balance member 62 need only be contoured on the underside to allow movement of the balance member. Deformable portion 66" may extend over the entire length of the balance member.

Referring again to FIG. 13, it will be noted that light structure 68 may emit light that forms a line. The emitted light may define a line via light incident on at least two points on the cast, such as a line defined by points 84a and 84b or a line defined by points 86a and 86b. Light source 72 may transmit light in the form of two points, such as by two vertically aligned light beams. However, in the example shown in FIG. 13, light source 72 transmits light in the form of a vertical line.

Figure 16:
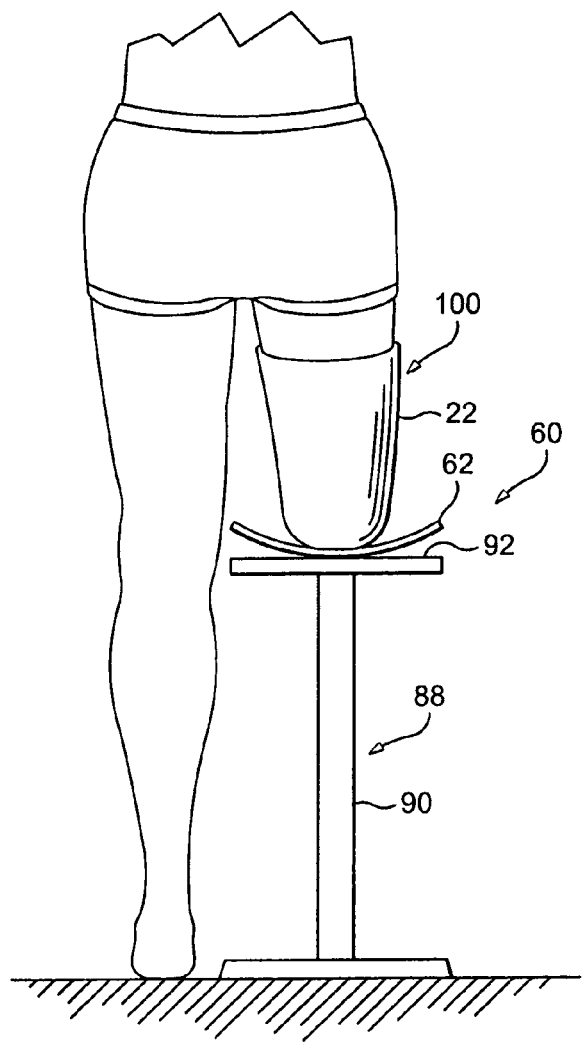
FIG. 16 is a rear view of an amputee with a cast-covered residual limb bearing on an exemplary alignment device, the alignment device being mounted on a height-adjustable support configured to accommodate placement of the cast in a balance orientation.

To determine the appropriate length of the prosthesis, alignment device 60 may include a height-adjustable support 88, as shown in FIG. 16. The height-adjustable support may take the form of a plurality of stackable blocks which may be arranged to establish a reference surface at any of a variety of levels based on a particular amputee's needs, or a height-adjustable table that has one or more telescoping leg(s) 90. Balance member 62 may be supported by the height-adjustable support and moved along a supporting surface thereof, such as top surface 92. For example, an amputee may stand with one leg next to the table and the cast-covered residual limb on balance member 62. The height of support 88 may be adjusted so that the user's hips are level when the cast-covered residual limb is resting on the balance member.

Once an amputee is standing with his or her residual limb on balance member 62, whether the amputee is in a position of standing postural balance may be verified by the prosthetist. The prosthetist may use alignment of landmarks on the amputee's body, such as the hips or spine, to determine an appropriate posture. Other devices may be used to assist in this process. For example, the prosthetist may align another light source with body structures that signify an anatomically neutral position, such as along the center of the face in the frontal plane. Upon achieving standing postural balance, the amputee's residual limb, and the cast covering such residual limb will be considered to have achieved a balance orientation.

Information regarding the balance orientation of the cast may be recorded by marking the cast with a balance line corresponding to the balance orientation. By marking the cast with intersecting balance planes, a balance axis may be identified, and a balance position on the cast defined. The balance position may be marked for subsequent socket alignment, such as for determining the appropriate position of an artificial shin structure relative to a socket assembly so that the prosthesis appropriately meets the weight bearing requirements of the amputee.

As noted, the balance axis and balance position may be defined by the intersection of two central planes. When the cast is in the balance orientation, each balance plane is a substantially vertical plane passing through the lowermost point of the cast when the cast is in the balance orientation and is bearing on the alignment device.

Figure 17:
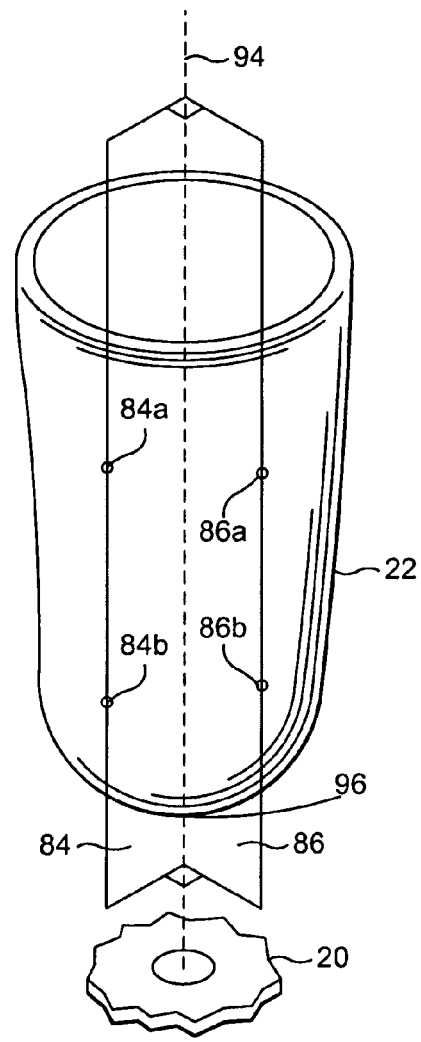
FIG. 17 is a perspective view of a cast with markings that designate a frontal plane and a sagittal plane on a cast, the frontal and sagittal planes defining an axis of intersection for use in alignment of prosthetic components on a prosthesis formed using the cast.

For example, as shown in FIGS. 13 and 17, the cast may be marked to record a first balance plane 84 in the form of a frontal plane, and a second balance plane 86 in the form of a sagittal plane. Although any two intersecting planes passing through the cast may be used, a frontal plane and a sagittal plane are anatomical planes identifiable to a clinician with reference to anatomical landmarks and thus are typically used.

In the depicted example of FIGS. 13 and 17, alignment markings, such as two points 84a, 84b along the front of the socket and two points 86a, 86b along the side of the cast, may be used to determine a first balance line and a second balance line, which correspond to intersecting first and second balance planes through the cast. The axis of intersection of these planes forms balance axis 94. Because the frontal plane and the sagittal plane are assumed to be substantially perpendicular, only two points on the cast are necessary to identify each balance plane. It will be appreciated that marking a third point for each plane (such as by using a second light source to mark a third point on the opposite side of the cast) would obviate the need for perpendicularity. Thus, in some embodiments, the amputee may stand with his or her cast-covered residual limb on balance member 62, between two light sources.

The location where balance axis 94 passes through the cast, and resulting socket, is referred to herein as balance position 96. Once balance axis 94 and balance position 96 have been determined, a prosthetic component, such as alignment block 20, may be assembled parallel to balance axis 94 and centered on balance position 96 to provide the amputee with a prosthetic device requiring minimal further adjustments.

As will be understood, alignment markings on cast 22 may be manually transferred to socket 14 for alignment of prosthetic components on the prosthesis. For example, prior to the cast being filled with plaster to create the positive limb model, a mandrel may be placed in the plaster and aligned with the alignment markings. A socket formed over this positive model may have alignment block 20, or other support structure, coupled in a location and orientation on the exterior distal end of the socket corresponding to the location and orientation of the mandrel. Thus, the prosthetic components may be properly aligned when coupled to the alignment block.

When the appropriate equipment is available, the alignment markings may be transferred to a computer system. For example, the alignment markings and/or cast geometry may be transferred to a computer system using a touch probe, laser, or photographic-based three-dimensional scanning system. A Computer-Aided Design and Manufacturing (CAD/CAM) system may be used to design the final socket and align the remaining prosthetic components.

Figure 18:
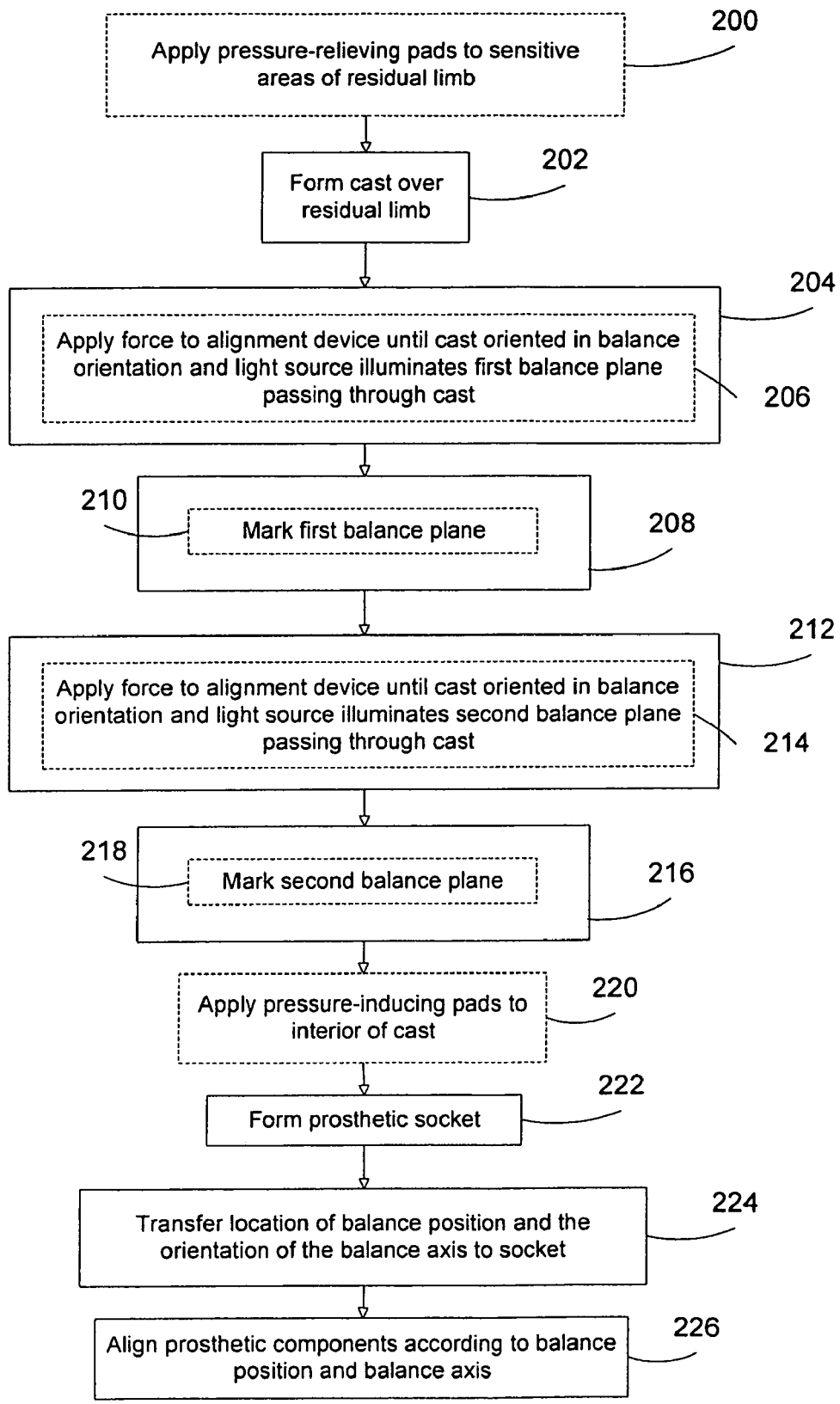
FIG. 18 is a flow diagram illustrating a method of forming and aligning a prosthetic device.

FIG. 18 generally illustrates the above described method. A prosthetist determines whether it is necessary to use pressure-relieving pads for a particular amputee, and may apply pressure-relieving pads to sensitive areas of the residual limb at 200. A cast is formed over the residual limb (including any pressure-relieving pads) at 202. The balance orientation is determined once the cast is formed 204. In determining the balance orientation, the cast may be positioned on the alignment device with a particular anatomical plane facing the light source. The height of the alignment device may be adjusted to assist in placing the amputee in an appropriate anatomically neutral posture. Further, the amputee may apply a force through the cast to the alignment device until the alignment device moves to indicate the amputee is in a position of standing postural balance and the cast is oriented in the balance orientation, with a light source illuminating a corresponding balance line on the cast at 206. Once the balance orientation is determined a first balance plane may be recorded at 208. In recording the first balance plane, the prosthetist may mark the plane directly on the cast at 210. The determining and recording steps may be repeated as needed until the three-dimensional location of the balance axis and balance position are found. For example, the balance orientation may be determined with a different anatomical plane facing the light source at 212. The light source then illuminates a second balance line at 214. A second balance plane thus may be recorded at 216.

Upon removing the cast from the residual limb, one or more pressure-inducing pads may be applied to the interior of the cast as necessary to provide an appropriate contour for the residual limb at 220. The cast may be used as a negative limb model to form a positive limb model, from which a prosthetic socket is formed at 222. The location of the balance position, and the orientation of the balance axis, may be transferred to the socket at 224, and the prosthetic components aligned accordingly for assembly of the prosthetic device at 226.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A method of recording information regarding a balance orientation of a limb-receiving member covering a residual limb of an amputee, the method comprising:

positioning the limb-receiving member in the balance orientation with the limb-receiving member bearing on a movable alignment device, wherein positioning the limb-receiving member includes positioning the limb-receiving member relative to the alignment device to align a first anatomical plane of the residual limb with the transmitted light; and transmitting light from the movable alignment device onto the limb-receiving member to define a first balance plane trough the limb-receiving member;

repositioning the limb-receiving member in the balance orientation with the limb-receiving member positioned relative to the alignment device to align a second anatomical plane of the residual limb with the transmitted light; and transmitting light from the movable alignment device onto the limb-receiving member to define a second balance plane through the limb-receiving member.

2. The method of claim 1, further comprising determining a balance axis defined by the intersection of the first balance plane and the second balance plane.

3. The method of claim 2, further comprising aligning a component of a prosthetic device with the balance axis.

4. The method of claim 1, further comprising applying one or more pressure pads to the interior of the limb-receiving member.

5. The method of claim 1, further comprising adjusting the height of the alignment device to accommodate positioning of the limb-receiving member in the balance orientation.

6. A method of preparing a prosthesis for an amputee having a lower extremity residual limb, comprising:

forming a cast on the residual limb;

positioning the cast in a first balance orientation with the cast bearing on an alignment device having a movable marker, the marker facing the cast to designate a first balance plane passing through the cast;

recording the first balance plane as indicated by the marker;

positioning the cast in a second balance orientation with the cast bearing on the alignment device with the marker facing the cast to designate a second balance plane passing through the cast;

recording the second balance plane as indicated by the marker;

determining an axis of intersection of the first balance plane and the second balance plane; and aligning a prosthetic component based on the axis of intersection.

7. The method of claim 6, further comprising applying one or more pressure-reducing pads to the residual limb before the cast is formed.

8. The method of claim 7, further comprising:

removing the cast from the residual limb;

applying one or more pressure-inducing pads to interior to the cast;

forming a positive limb model based on the cast and pressure-inducing pads; and forming a prosthetic socket based on the positive limb model.

9. The method of claim 8, wherein aligning a prosthetic component includes coupling an artificial shin structure to the socket in alignment with the axis of intersection.

10. The method of claim 6, wherein recording the first central plane and the second central plane includes marking a line in each plane on the cast.

* * * * *